US012714401B2

(12) United States Patent
Kijanka et al.

(10) Patent No.: US 12,714,401 B2
(45) Date of Patent: Aug. 25, 2026

(54) SHEAR WAVE PHASE VELOCITY ESTIMATION WITH EXTENDED BANDWIDTH USING GENERALIZED STOCKWELL TRANSFORM AND SLANT FREQUENCY WAVENUMBER ANALYSIS

(71) Applicants: Mayo Foundation for Medical Education and Research, Rochester, MN (US); Akademia Gorniczo-Hutnicza Im. Stanislawa Staszica W Krakowie, Cracow (PL)

(72) Inventors: Piotr Kijanka, Cracow (PL); Matthew W. Urban, Rochester, MN (US)

(73) Assignees: Mayo Foundation for Medical Education and Research, Rochester, MN (US); Akademia Gorniczo-Hutnicza Im. Stanislawa Stanszica W Krakowie, Cracow (PL)

( * ) Notice: Subject to any disclaimer, the term of this patent is extended or adjusted under 35 U.S.C. 154(b) by 438 days.

(21) Appl. No.: 18/262,345

(22) PCT Filed: Jan. 24, 2022

(86) PCT No.: PCT/US2022/013463
§ 371 (c)(1),
(2) Date: Jul. 20, 2023

(87) PCT Pub. No.: WO2022/159794
PCT Pub. Date: Jul. 28, 2022

(65) Prior Publication Data

US 2024/0074734 A1 Mar. 7, 2024

Related U.S. Application Data

(60) Provisional application No. 63/140,590, filed on Jan. 22, 2021.

(51) Int. Cl.
*A61B 8/00* (2006.01)
*G01R 33/48* (2006.01)

(52) U.S. Cl.
CPC ............ *A61B 8/485* (2013.01); *A61B 8/5207* (2013.01); *A61B 8/54* (2013.01); *G01R 33/4814* (2013.01)

(58) Field of Classification Search
None
See application file for complete search history.

(56) References Cited

U.S. PATENT DOCUMENTS

| | | | |
|---|---|---|---|
| 2017/0103537 | A1 | 4/2017 | Cheng et al. |
| 2021/0018606 | A1 | 1/2021 | McCaw et al. |
| 2021/0341429 | A1 | 11/2021 | Kijanka et al. |

OTHER PUBLICATIONS

Askari, Roohollah, and Robert J. Ferguson. "Dispersion and the dissipative characteristics of surface waves in the generalized S-transform domain." Geophysics 77.1 (2012): V11-V20.

(Continued)

*Primary Examiner* — Mark R Milia
(74) *Attorney, Agent, or Firm* — Quarles & Brady LLP

(57) ABSTRACT

Shear wave phase velocity is estimated from measurements of shear wave motion obtained using ultrasound shear wave elastography or other suitable elastography techniques. Shear wave dispersion curves are generated using a combined generalized Stockwell transform and slant wave number-frequency analysis. A modified version of the S-transform is used to control the time-frequency resolution of a time-frequency decomposition of a signal.

22 Claims, 5 Drawing Sheets

(56) References Cited

OTHER PUBLICATIONS

Kijanka, Piotr, and Matthew W. Urban. "Phase velocity estimation with expanded bandwidth in viscoelastic phantoms and tissues." IEEE transactions on medical imaging 40.5 (2021): 1352-1362.
Pinnegar, C. Robert, and Lalu Mansinha. "The S-transform with windows of arbitrary and varying shape." Geophysics 68.1 (2003): 381-385.
Serdyukov, Aleksander S., et al. "Slant f—k transform of multichannel seismic surface wave data." Geophysics 84.1 (2019): A19-A24.
Stockwell, Robert Glenn, Lalu Mansinha, and R. P. Lowe. "Localization of the complex spectrum: the S transform." IEEE transactions on signal processing 44.4 (1996): 998-1001.
PCT International Search Report and Written Opinion, PCT/US2022/013463, mailed on Apr. 19, 2022, 15 pages.

SHEAR WAVE PHASE VELOCITY ESTIMATION WITH EXTENDED BANDWIDTH USING GENERALIZED STOCKWELL TRANSFORM AND SLANT FREQUENCY WAVENUMBER ANALYSIS

CROSS-REFERENCE TO RELATED APPLICATIONS

This application represents the national stage entry of PCT/US2022/013463 filed on Jan. 24, 2022 and claims the benefit of U.S. Provisional Patent Application Ser. No. 63/140,590, filed on Jan. 22, 2021, and entitled "SHEAR WAVE PHASE VELOCITY ESTIMATION WITH EXTENDED BANDWIDTH USING GENERALIZED STOCKWELL TRANSFORM AND SLANT FREQUENCY WAVENUMBER ANALYSIS," which is herein incorporated by reference in its entirety.

STATEMENT REGARDING FEDERALLY SPONSORED RESEARCH

This invention was made with government support under DK092255 awarded by the National Institutes of Health. The government has certain rights in the invention.

BACKGROUND

Ultrasound shear wave elastography ("SWE") has been used in numerous clinical applications in order to make noninvasive, quantitative measurements of different mechanical properties in soft tissues. Among the many ultrasound-based elastography methods are those that utilize acoustic radiation force ("ARF"). After the ARF is applied, a propagating shear wave results from the perturbation of the medium. For estimation of the shear wave motion, ultrafast ultrasound imaging techniques can then be applied for data recording. Next, shear wave velocity is estimated, which is related to the mechanical properties of the tissue, using various techniques.

Many SWE approaches consider tissue to be strictly elastic while ignoring viscous properties. It has been shown that ignoring tissue viscosity results in elasticity measurement bias. One characteristic of viscoelastic materials is that the shear wave phase velocity varies with frequency, which is referred to as dispersion. Viscoelastic properties of tissues can be estimated by fitting the shear wave dispersion curves to a rheological model. They can also be evaluated using data driven techniques.

Shear wave phase velocity dispersion has been measured in many different applications. Measurement of the phase velocity dispersion curve has commonly been carried out with either a phase gradient or a two-dimensional Fourier transform ("2D-FT"). Other approaches used for shear wave phase velocity calculation include a Radon sum method, a multiple-signal classification ("MUSIC") approach, and a two-point continuous wavelet transform ("2P-CWT"). However, with these shear wave phase velocity measurement methods, the main drawback is the resulting frequency bandwidth. Differentiation of viscoelastic tissues can be accomplished when higher frequencies can be used, so maximization of the bandwidth for computing the dispersion curves is essential.

The 2D-FT methods, which transform spatiotemporal data (x, t) to wavenumber-frequency (k, f) domain, have been used to measure the dispersion. The peaks of the magnitude distribution of the (k, f) spectrum are used to measure the phase velocities using the relationship $c=2\pi f/k$. Estimated dispersion curves either from the phase gradient, 2D-FT, or other technique can be fit to rheological models to evaluate the viscoelastic parameters of the medium.

SUMMARY OF THE DISCLOSURE

The present disclosure addresses the aforementioned drawbacks by providing a method for generating shear wave phase velocity data from ultrasound data obtained with an ultrasound system. Ultrasound data are accessed with a computer system, the ultrasound data being representative of shear wave motion in a region-of-interest in a subject. Time-frequency-space domain data are generated with the computer system by applying a Stockwell transform to the ultrasound data, and a slant-phase function is generated from the time-frequency-space domain data. Slant-phase amplitude values are computed with the computer system using the slant-phase function, and phase velocity dispersion curve data are then generated from the slant-phase amplitude values.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
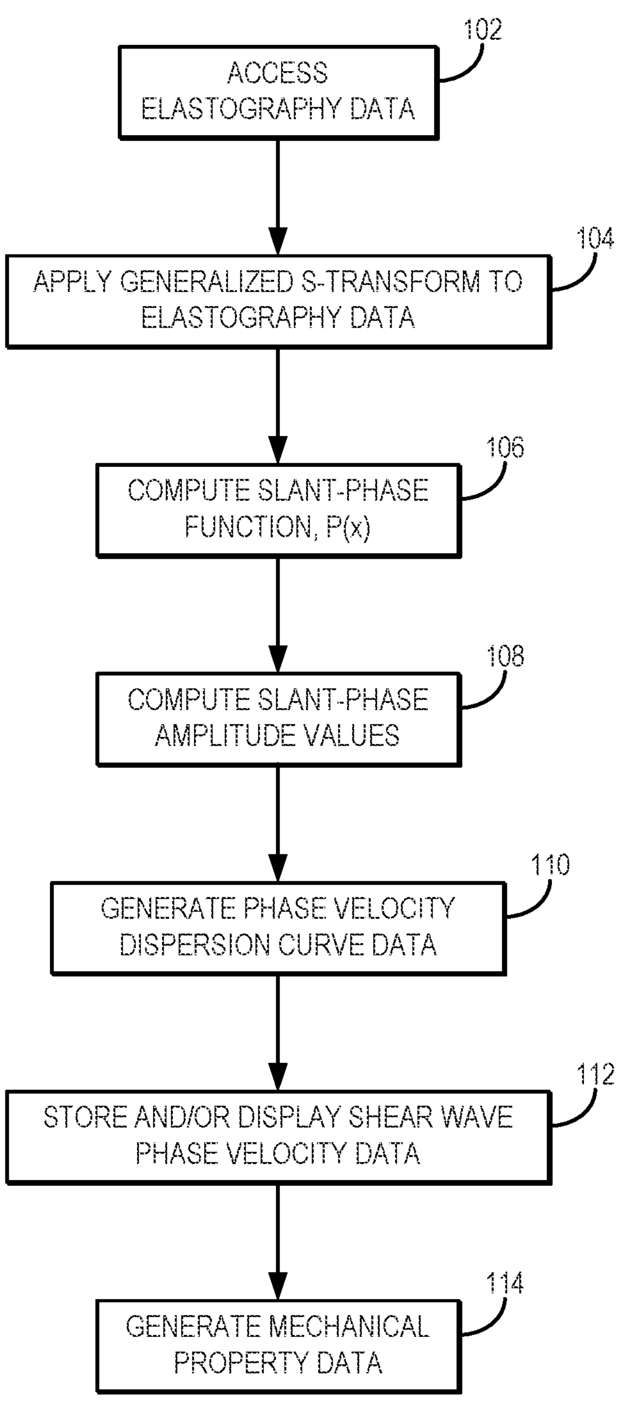
FIG. 1 is a flowchart setting forth the steps of an example method for estimating shear wave phase velocity using a slant frequency wavenumber generalized S-transform based technique to estimate dispersion curves.

Described here are systems and methods for estimating shear wave phase velocity from measurements of shear wave motion obtained using ultrasound shear wave elastography or other suitable elastography techniques, including magnetic resonance elastography ("MRE") or optical based elastography techniques, such as optical coherence tomography ("OCT") based elastography. In general, shear wave dispersion curves are generated using a combined technique of a generalized Stockwell transform ("S-transform") and a slant wavenumber-frequency analysis. A modified version of the S-transform is used to control the time-frequency resolution of a time-frequency decomposition of a signal.

The technique implemented in the present disclosure may be referred to as GST-SFK (generalized Stockwell transformation combined with a slant frequency-wavenumber analysis) enables shear wave velocity dispersion curves to be obtained across a larger frequency bandwidth than previously achieved. For instance, the GST-SFK technique described in the present disclosure provides an expanded bandwidth by a factor of two or more to be used for phase velocity estimation, which is meaningful for a tissue dispersion analysis in vivo. Advantageously, this larger frequency bandwidth allows for the differentiation between some soft tissues where existing methods cannot, and therefore allows for more accurate diagnosis of potential diseases to be obtained.

The systems and methods described in the present disclosure thus provide advantages over previous approaches for estimating shear wave phase velocity in elastography techniques. For instance, the systems and methods improve on previous eigenvector and/or multiple signal classification techniques by enabling a larger bandwidth for the dispersion curves. Advantageously, having dispersion curves over a wider frequency range also allows for a more accurate estimate of the viscoelastic parameters.

In conventional two-dimensional Fourier transform ("2D-FT") based methods, the frequency-wavenumber ("f-k") domain distribution of ultrasound shear wave axial particle velocity motion data measured at different lateral locations can be processed in a way that a 2D-FT performed in temporal and spatial domains can create a frequency-wavenumber distribution. Phase velocity curves can then be computed by finding the peaks in the f-k distribution. From the 2D f-k maps, peaks can be detected for each frequency. In order to extract the main shear wave mode from the detected peaks, the peaks corresponding to the shear wave mode can be tracked by searching for the nearest value. The coordinates of the localized peaks can be used to calculate the phase velocity as $c=2\pi f/k$.

Conventional eigenvector ("EV") based approaches are associated with the MUSIC method. They allow for asymptotically unbiased estimates of a general set of signal parameters. For example, the EV approach, like MUSIC, is based on the orthogonality between signal and noise subspaces spanned by the eigenvectors of the correlation matrix. Using the noise subspace eigenvectors (i.e., M-p eigenvectors) the power spectrum of a signal can be computed through the following equation $$\hat{P}_{EV}(e^{j\omega}) = \frac{1}{\sum_{i=p+1}^{M} \frac{1}{\lambda_i}\left|\bar{e}^H \bar{v}_i\right|^2}; \tag{1}$$

where, $\bar{e}$ is the vector of complex exponentials, $e^{j\omega}$, and $\lambda_i$ is the eigenvalue associated with the eigenvector, $\bar{v}_i$. The superscript "H" indicates the Hermitian operator. The eigenvectors, $\bar{v}_i$, coincide with the M-p smallest eigenvalues that span the noise subspace, where M is the size of the autocorrelation matrix and p is a number of complex exponentials in white noise.

The EV method and the MUSIC algorithm are distinct in a way that MUSIC uses unity weighting, whereas EV applies inverse eigenvalues. Hence, the MUSIC algorithm yields more spurious peaks than the EV method. EV is considered to shape the noise spectrum better than MUSIC. The constant p=1 can be selected when one propagating shear wave mode is expected to be found in the examined bulk media. The parameter M=128 can be selected based on an assumption related to the influence of the autocorrelation matrix size on the dispersion curves calculation.

The Stockwell transform, referred to as the S-transform, produces a time-frequency decomposition of a signal with a frequency-dependent Gaussian window used for spectral localization. The Gaussian window width scales inversely, and its height scales linearly, with the frequency controlling the time-frequency resolution. The S-transform, in its original form, can be given as:

$$S[h(\tau)](\tau, f) = \int_{-\infty}^{+\infty} h(t)\left[\frac{|f|}{\sqrt{2\pi}} e^{-\frac{f^2(\tau-t)^2}{2}}\right] e^{-i2\pi ft} dt; \tag{2}$$

where S denotes the time-frequency S-transform of the time variable signal, h(t), where f is a frequency and $\tau$ is a parameter that controls the position of the Gaussian window on the time vector, t.

The systems and methods described in the present disclosure make use of a generalized S-transform to manipulate the time-frequency resolution. In this generalized form, the Gaussian window is replaced with a generalized window as:

$$S[h(\tau)](\tau, f, \beta) = \int_{-\infty}^{+\infty} h(t) w(\tau - t, f, \beta) e^{-i2\pi ft} dt \tag{3}$$

where, w is the scaled Gaussian window, which can be given as:

$$w(\tau - t, f, \beta) = \frac{|f|}{\sqrt{2\pi\beta}} e^{-\frac{f^2(\tau-t)^2}{2\beta}} \tag{4}$$

where, $\beta$ is a scaling factor. After substituting Eqn. (4) into Eqn. (3), the generalized S-transform becomes:

$$S[h(\tau)](\tau, f, \beta) = \int_{-\infty}^{+\infty} h(t)\left[\frac{|f|}{\sqrt{2\pi\beta}} e^{-\frac{f^2(\tau-t)^2}{2\beta}}\right] e^{-i2\pi ft} dt. \tag{5}$$

The scaling factor, $\beta$ changes the width of the window and controls the time-frequency resolution by altering the number of oscillations in the window. A narrower window in the time domain widens in the frequency domain, reducing frequency resolution. For larger $\beta$ values, the Gaussian window is widened in the time domain, thereby increasing the frequency resolution. In general, values of $\beta$ that are less than $\beta=1$ and greater than $\beta=0$ can be used (i.e., $\beta$ can be selected from the range $0<\beta<1$). For instance, in some implementations a value of $\beta=0.3$ may be used. In other implementations, a value of $\beta=0.5$ may be used. In general, the value of $\beta$ can be selected based on considerations of the desired time-frequency resolution for a particular application. In still other embodiments, other versions of the generalized S-transform can also be used, including other versions of the generalized S-transform with one or more scaling factors.

A shear wave wavefield, h(x, t), can be transformed using the generalized S-transform to the time-frequency domain described above. For a selected frequency range, a series of 2D complex-valued functions of the time and distance can be obtained, which can be written as:

$$H(x, \tau) = S[h(x, t)](\tau, f, x). \quad (6)$$

By taking slant slices of the H(x, τ) function, for a selected frequency, f, and steering group velocity, u=x/τ, and the constant time, the one-dimensional complex-valued, slant-phase function, P, can be considered in the following form:

$$P(x) = H\left(x, \frac{x}{u_m} = \tau\right) \text{ for } u_m = \frac{x_m}{t_m - m\Delta t}. \quad (7)$$

The P function is computed for a series of steering group velocity values, $u_m$, where Δt is the time sampling rate; for a maximum distance, $x_m$; and for a maximum time, $t_m$, of the recorded shear wave motion data. Then, the amplitude of the P function can be computed as:

$$\Lambda(u, f, k) = \left| \int_{-\infty}^{+\infty} P(x) e^{-2i\pi kx} dx \right|; \quad (8)$$

which is a three-dimensional spectral amplitude distribution with the coordinates of the steering group velocity, frequency, and wavenumber. The spectral amplitude peaks of the P function correspond to the distribution of the wavenumbers of elastic waves, which travel away from the source. To obtain the dispersion curves, a maximum amplitude of Λ(u, f, k) over all of the steering group velocities is evaluated, which can be written as:

$$K(f, k) = \max_u [\Lambda(u, f, k)]. \quad (9)$$

The peaks of K(f, k) for an impulsive ARF push are related to the phase velocities of different wave propagation modes. Phase velocity curves can be computed from finding the peaks in the K(f, k) distribution. These peaks can be found at each frequency, f, by searching in an orthogonal direction along the k-direction. Then, the phase velocity mode curves for the main shear wave mode can be localized in a similar way as for the 2D-FT method described above.

Referring now to FIG. 1, a flowchart is illustrated as setting forth the steps of an example method for estimating shear wave velocity using a slant frequency wavenumber generalized S-transform based technique to estimate dispersion curves.

The method includes accessing elastography data with a computer system, as indicated at step 102. Accessing the data can include retrieving previously acquired data from a memory or other suitable data storage device or media in communication with the computer system. Additionally or alternatively, accessing the data can include acquiring the data with an imaging system and transferring or otherwise communicating the data with the computer system, which in some instances may be a part of the imaging system.

As a non-limiting example, the elastography data may be ultrasound data acquired with an ultrasound system. In some other embodiments, the elastography data may instead be other elastography data that are representative of shear wave motion, including magnetic resonance elastography data acquired using an MRI system, optical elastography data acquired using an optical coherence tomography system, or other suitable elastography data.

In some embodiments, the elastography data may be ultrasound data that are spatiotemporal data representative of shear wave motion, and thus may in some instances also be referred to as shear wave motion data. The shear wave motion data may be two-dimensional, or higher dimensional (e.g., three-dimensional, four-dimensional) data. The shear wave motion data may be shear wave particle displacement motion data, shear wave particle velocity motion data, or the like. Thus, in one non-limiting example the ultrasound data can include 2D shear wave particle velocity motion data, which may be represented as (x, t).

The ultrasound data may be acquired at a single depth (e.g., an ARF depth), or alternatively may be acquired at multiple different depths, whether simultaneously or sequentially.

The ultrasound or other elastography data are then transformed into a 3D time-frequency-space domain (t, f, x), as indicated at step 104. For instance, the ultrasound or other elastography data can be transformed using a generalized S-transform, such as the one shown in Eqn. (5), and as described above. In these instances, transforming the ultrasound or other elastography data may include setting or otherwise accessing preset parameters for the transform operation, such as the scaling parameter, β. In general, the scaling parameter can be selected from the range 0<β<1, such as β=0.3, β=0.5, or other suitable values. In some implementations, an S-transform other than the generalized S-transform may also be used. In these instances, the user may also select a window function to be utilized in the S-transform. The window function may be selected based on the particular application.

A slant frequency wavenumber analysis is then performed on the time-frequency-space domain data in order to compute a slant-phase function, P, as indicated at step 106. For instance, the slant-phase function can be computed using Eqn. (7) as described above. Slant-phase amplitude values, Λ(u, f, k), are then computed from the slant-phase function, as indicated at step 108. For instance, the slant-phase amplitude values, Λ(u, f, k), can be computed using Eqn. (8) as described above.

Phase velocity dispersion curve data are then generated based on searching for one or more maximum amplitude values in the slant-phase amplitude values, Λ(u, f, k), over all steering group velocities, u, as indicated at step 110. For instance, frequency-wavenumber pairs, K(f, k) can be determined from the slant-phase amplitude values, Λ(u, f, k), using Eqn. (9) and then dispersion curves can be generated according to c(f)=f/k.

Figure 2A:
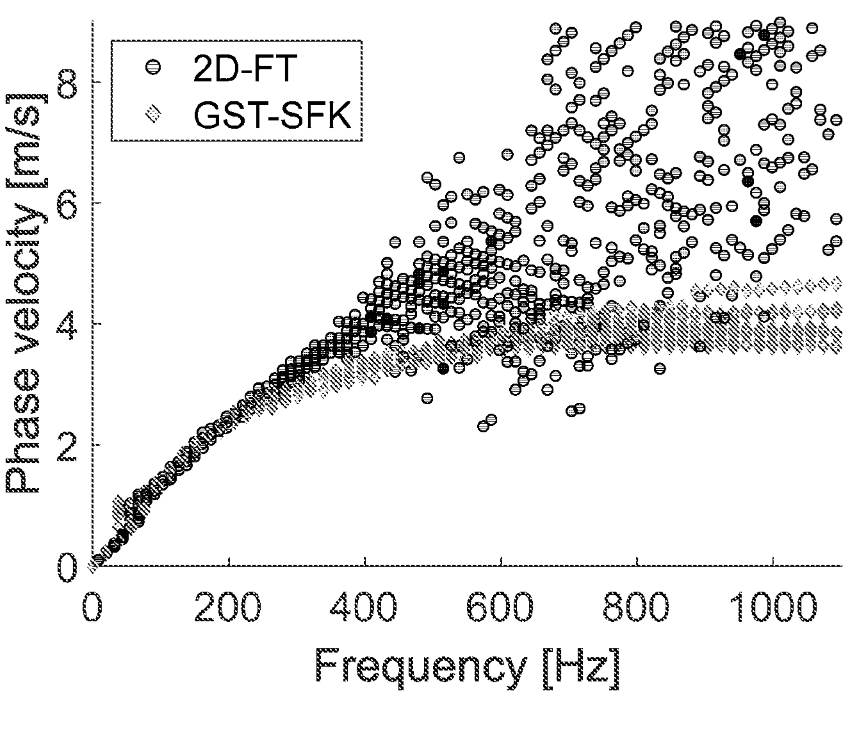
FIG. 2A shows example dispersion curves estimated using the systems and methods described in the present disclosure ("GST-SFK") as compared to dispersion curves estimating from the same data using a 2D-FT based technique.
Figure 2B:
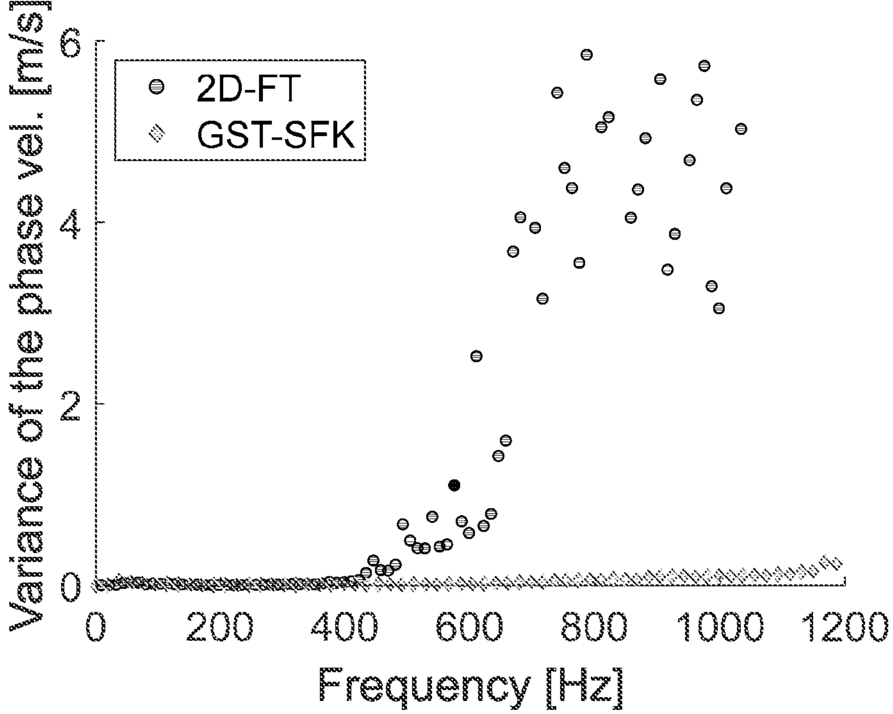
FIG. 2B illustrates the variance of the phase from the measurements shown in FIG. 2A.

The dispersion curve data can be stored as shear wave phase velocity data for later use or displayed to a user, as indicated at step 112. For example, the shear wave phase velocity data may be displayed to the user as shear wave phase velocity maps, which depict the spatial distribution of the measured shear wave phase velocity values within the imaged region-of-interest. Referring to FIGS. 2A and 2B, an example of dispersion curves estimated using the methods described in the present disclosure are shown. FIG. 2A shows example dispersion curves estimated using the methods described in the present disclosure ("GST-SFK") in comparison to dispersion curves estimates using a 2D-FT based method. The dispersion curves were estimated from ultrasound shear wave elastography experiments in renal transplants. The associated variance of the phase velocity versus frequency is shown in FIG. 2B, and for the GST-SFK method the variance is lower over a larger frequency range than for the 2D-FT method.

Additionally or alternatively, the shear wave phase velocity data may be further processed to generate mechanical property data, as indicated at step 114. These mechanical property data may also be stored for later use and/or displayed to the user. As one non-limiting example, the mechanical property data can include quantitative values of mechanical properties of the tissues or other media in the imaged region-of-interest. Such values can be presented to a user in a report, which in some embodiments may include a print-out and/or display that is generated for the user. As another non-limiting example, the mechanical property data can include mechanical property maps, which depict a spatial distribution of the computed mechanical property values within the imaged region-of-interest. For instance, a mechanical property map can be an image whose pixel values are set as, or otherwise correspond to, a computed mechanical property. Examples of mechanical properties include viscoelastic parameters.

The systems and methods described in the present disclosure provide a GST-SFK method for robust calculation of shear wave phase velocity in soft media and tissues. In one example study, the GST-SFK approach was evaluated with shear wave particle velocity data induced by ARF in viscoelastic media using numerical models. The GST-SFK approach is capable of outperforming other techniques, such as by giving robust dispersion curves for much longer frequency range, up to approximately 2000 Hz, in comparison to the other techniques. In this way, the usable bandwidth can be extended more than two times, which can be used in differentiation of viscoelastic materials at higher frequencies where separation may be more distinct due to dispersion.

High-resolution methods, like the EV approach, do not yield true power spectral density estimates as they do not preserve process power between the time and frequency domains. The 2D-FT and GST-SFK methods do yield true power spectral density estimates (i.e., the frequency-wavenumber (f-k) distribution), and this information can be used for further processing if needed.

The GST-SFK method uses spectral decomposition combined with slant frequency wavenumber analysis. It uses the S-transform which combines strengths of the short-time Fourier transform ("STFT") and the continuous wavelet transform ("CWT") methods, and overcomes their shortcomings. The STFT can only be used in single resolution analysis and exhibits spectral smearing due to windowing. In addition, due to the fixed window width it cannot follow the signal dynamics correctly. The CWT is a multi-resolution method; however, it produces a time-scale decomposition rather than a time-frequency decomposition. Furthermore, its temporal resolution is a function of frequency and is controlled by the range of the analyzing wavelets.

The S-transform on the other hand, is a multi-resolution method. The S-transform of a function, h(t), is defined as a CWT with a particular mother wavelet multiplied by a phase factor. The S-transform provides an extension of instantaneous frequency to broadband signals. The phase of the S-transform referenced to the time origin provides additional information about spectra that is not available from locally referenced phase information in the CWT. For instance, the S-transform contains phase factors that refer to local phase information of each signal component. Phase measured by the S-transform is the localized value of absolute phase with respect to the Fourier spectrum. The GST-SFK method described in the present disclosure uses the amplitude and phase spectrum of the S-transform, which enables the estimation of the shear wave phase velocity.

Another advantage of the GST-SFK approach described in the present disclosure is that the S-transform may be constructed using windows other than a generalized window function, such as a Gaussian or other window function. Hence, it is possible to design windows better suited to certain applications to improve temporal resolution, if needed. Moreover, the S-transform can simultaneously estimate the local amplitude spectrum and the local phase spectrum.

In addition, the GST-SFK method described in the present disclosure uses the slant frequency-wavenumber transform to transform the data from the time-space domain to the frequency-phase velocity domain. By using the generalized S-transform, noise is excluded in the other time steps, which reduces spatial-spectral leakage artifacts. Thus, the presented approach outperforms the 2D-FT and EV techniques and provides much more robust phase velocity estimates with expanded bandwidth.

Because, the GST-SFK method preserves power spectral density estimates, it can advantageously be combined with other techniques, such as the local phase velocity based imaging ("LPVI") techniques described in co-pending PCT Application No. US2019/048519, which is herein incorporated by reference in its entirety.

Figure 3:
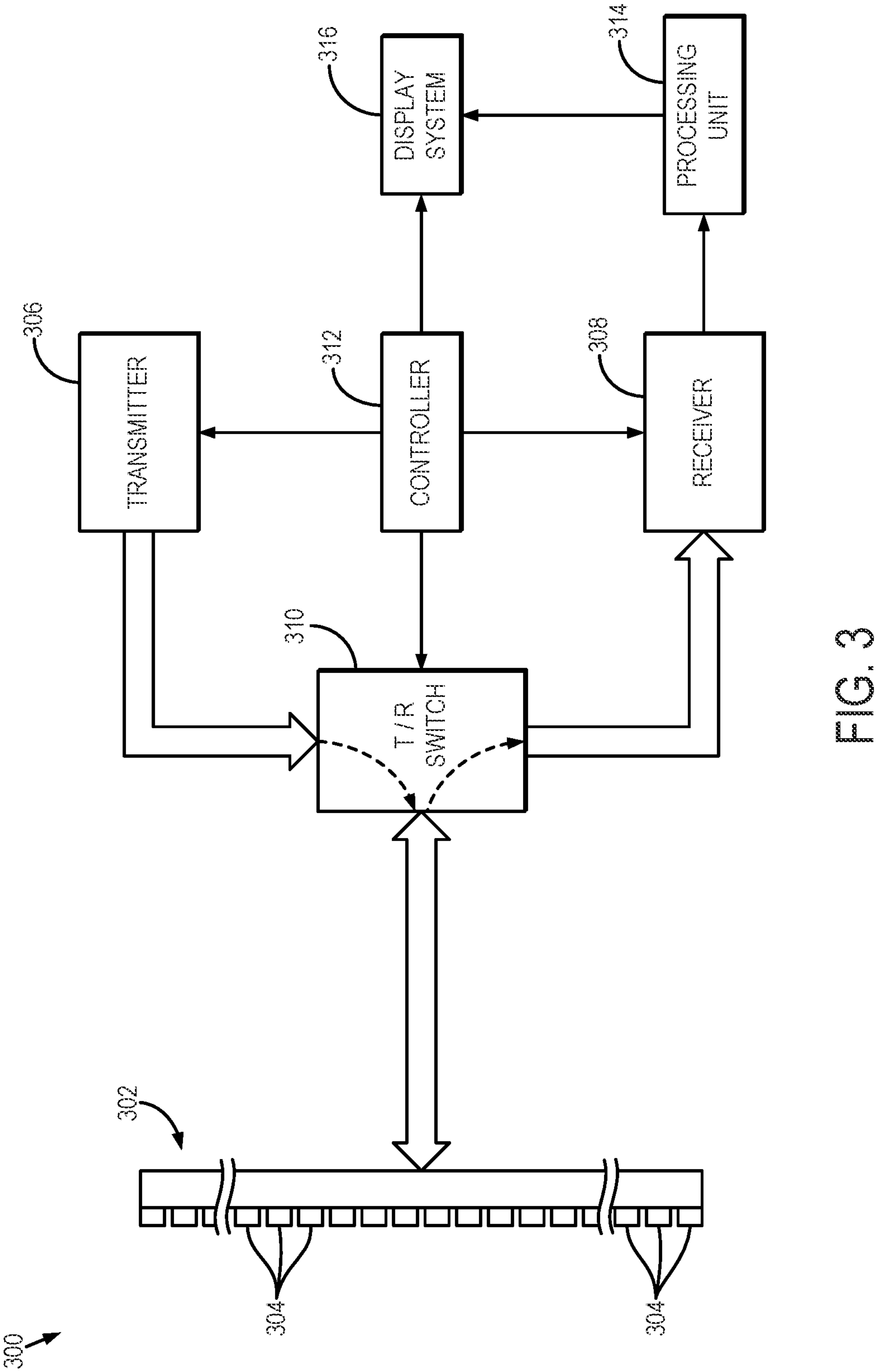
FIG. 3 is a block diagram of an example ultrasound system that can implement the methods described in the present disclosure.

FIG. 3 illustrates an example of an ultrasound system 300 that can implement the methods described in the present disclosure. The ultrasound system 300 includes a transducer array 302 that includes a plurality of separately driven transducer elements 304. The transducer array 302 can include any suitable ultrasound transducer array, including linear arrays, curved arrays, phased arrays, and so on. Similarly, the transducer array 302 can include a 1D transducer, a 1.5D transducer, a 1.75D transducer, a 2D transducer, a 3D transducer, and so on.

When energized by a transmitter 306, a given transducer element 304 produces a burst of ultrasonic energy. The ultrasonic energy reflected back to the transducer array 302 (e.g., an echo) from the object or subject under study is converted to an electrical signal (e.g., an echo signal) by each transducer element 304 and can be applied separately to a receiver 308 through a set of switches 310. The transmitter 306, receiver 308, and switches 310 are operated under the control of a controller 312, which may include one or more processors. As one example, the controller 312 can include a computer system.

The transmitter 306 can be programmed to transmit unfocused or focused ultrasound waves. In some configurations, the transmitter 306 can also be programmed to transmit diverged waves, spherical waves, cylindrical waves, plane waves, or combinations thereof. Furthermore, the transmitter 306 can be programmed to transmit spatially or temporally encoded pulses.

The receiver 308 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 306 and the receiver 308 can be programmed to implement a high frame rate. For instance, a frame rate associated with an acquisition pulse repetition frequency ("PRF") of at least 100 Hz can be implemented. In some configurations, the ultrasound system 300 can sample and store at least one hundred ensembles of echo signals in the temporal direction.

The controller 312 can be programmed to implement an imaging sequence as known in the art. In some embodiments, the controller 312 receives user inputs defining various factors used in the design of the imaging sequence.

A scan can be performed by setting the switches 310 to their transmit position, thereby directing the transmitter 306 to be turned on momentarily to energize transducer elements 304 during a single transmission event according to the prescribed imaging sequence. The switches 310 can then be set to their receive position and the subsequent echo signals produced by the transducer elements 304 in response to one or more detected echoes are measured and applied to the receiver 308. The separate echo signals from the transducer elements 304 can be combined in the receiver 308 to produce a single echo signal.

The echo signals are communicated to a processing unit 314, which may be implemented by a hardware processor and memory, to process echo signals or images generated from echo signals. As an example, the processing unit 314 can generate shear wave phase velocity data and/or mechanical property data using the methods described in the present disclosure. Images produced from the echo signals by the processing unit 314 can be displayed on a display system 316, in addition to the generated phase velocity data and/or mechanical property data, which as described above may include shear wave phase velocity maps and/or mechanical property maps.

Figure 4:
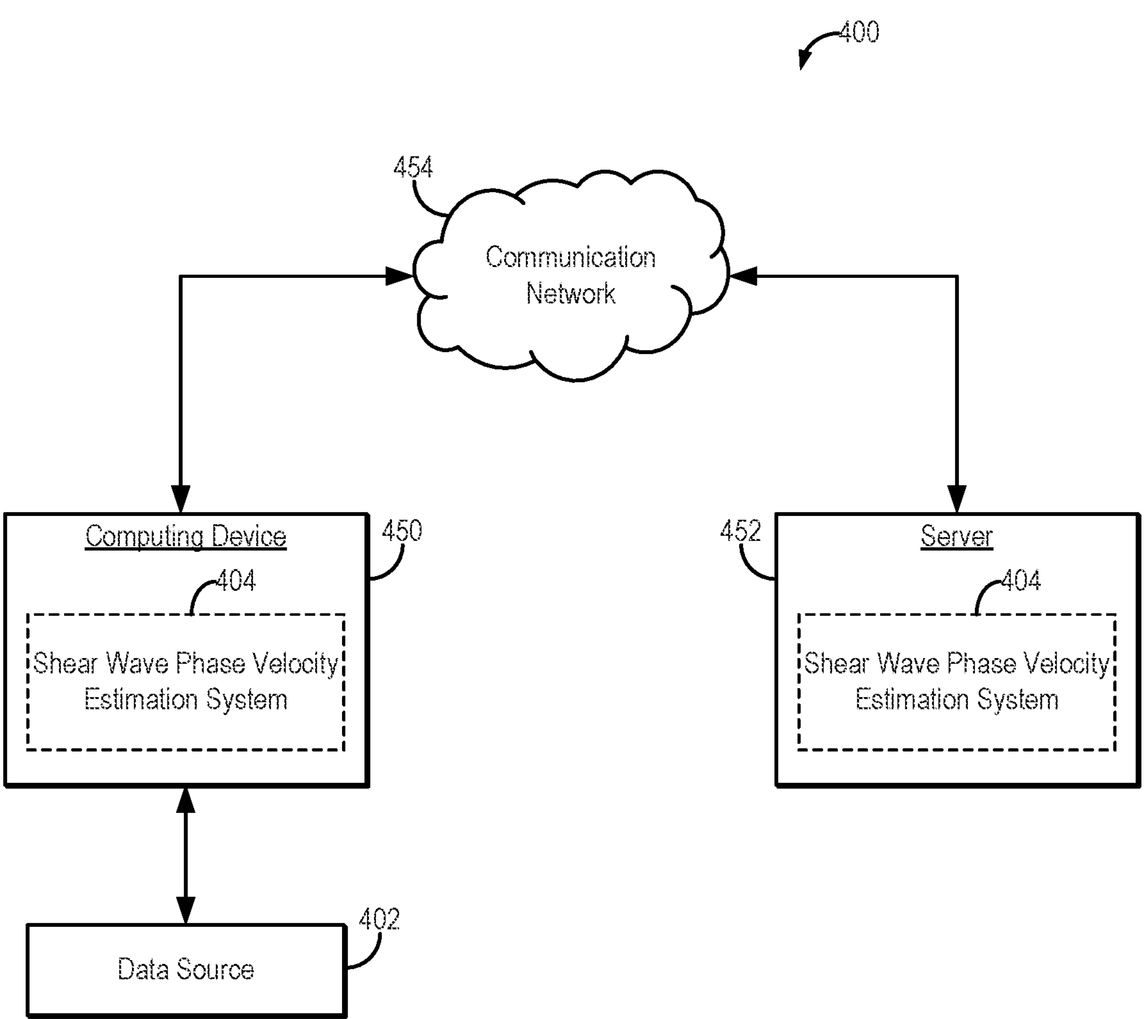
FIG. 4 is a block diagram of an example shear wave phase velocity estimation system.

Referring now to FIG. 4, an example of a system 400 for estimating shear wave phase velocity in accordance with some embodiments of the systems and methods described in the present disclosure is shown. As shown in FIG. 4, a computing device 450 can receive one or more types of data (e.g., ultrasound data, shear wave motion data, other elastography data) from data source 402, which may be an ultrasound data source, a magnetic resonance elastography data source, an OCT data source, or other elastography data source. In some embodiments, computing device 450 can execute at least a portion of a shear wave phase velocity estimation system 404 to estimate shear wave phase velocity data and/or mechanical property data from data received from the data source 402.

Additionally or alternatively, in some embodiments, the computing device 450 can communicate information about data received from the data source 402 to a server 452 over a communication network 454, which can execute at least a portion of the shear wave phase velocity estimation system 404. In such embodiments, the server 452 can return information to the computing device 450 (and/or any other suitable computing device) indicative of an output of the shear wave phase velocity estimation system 404.

In some embodiments, computing device 450 and/or server 452 can be any suitable computing device or combination of devices, such as a desktop computer, a laptop computer, a smartphone, a tablet computer, a wearable computer, a server computer, a virtual machine being executed by a physical computing device, and so on. The computing device 450 and/or server 452 can also reconstruct images from the data.

In some embodiments, data source 402 can be any suitable source of image data (e.g., measurement data, images reconstructed from measurement data), such as an ultrasound system, a magnetic resonance imaging system (e.g., an MRI system configured to implement magnetic resonance elastography), an optical imaging system (e.g., an OCT system configured to acquire elastography data), another computing device (e.g., a server storing image data), and so on. In some embodiments, data source 402 can be local to computing device 450. For example, data source 402 can be incorporated with computing device 450 (e.g., computing device 450 can be configured as part of a device for capturing, scanning, and/or storing images). As another example, data source 402 can be connected to computing device 450 by a cable, a direct wireless link, and so on. Additionally or alternatively, in some embodiments, data source 402 can be located locally and/or remotely from computing device 450, and can communicate data to computing device 450 (and/or server 452) via a communication network (e.g., communication network 454).

In some embodiments, communication network 454 can be any suitable communication network or combination of communication networks. For example, communication network 454 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 454 can be a local area network, a wide area network, a public network (e.g., the Internet), a private or semi-private network (e.g., a corporate or university intranet), any other suitable type of network, or any suitable combination of networks. Communications links shown in FIG. 4 can each be any suitable communications link or combination of communications links, such as wired links, fiber optic links, Wi-Fi links, Bluetooth links, cellular links, and so on.

Figure 5:
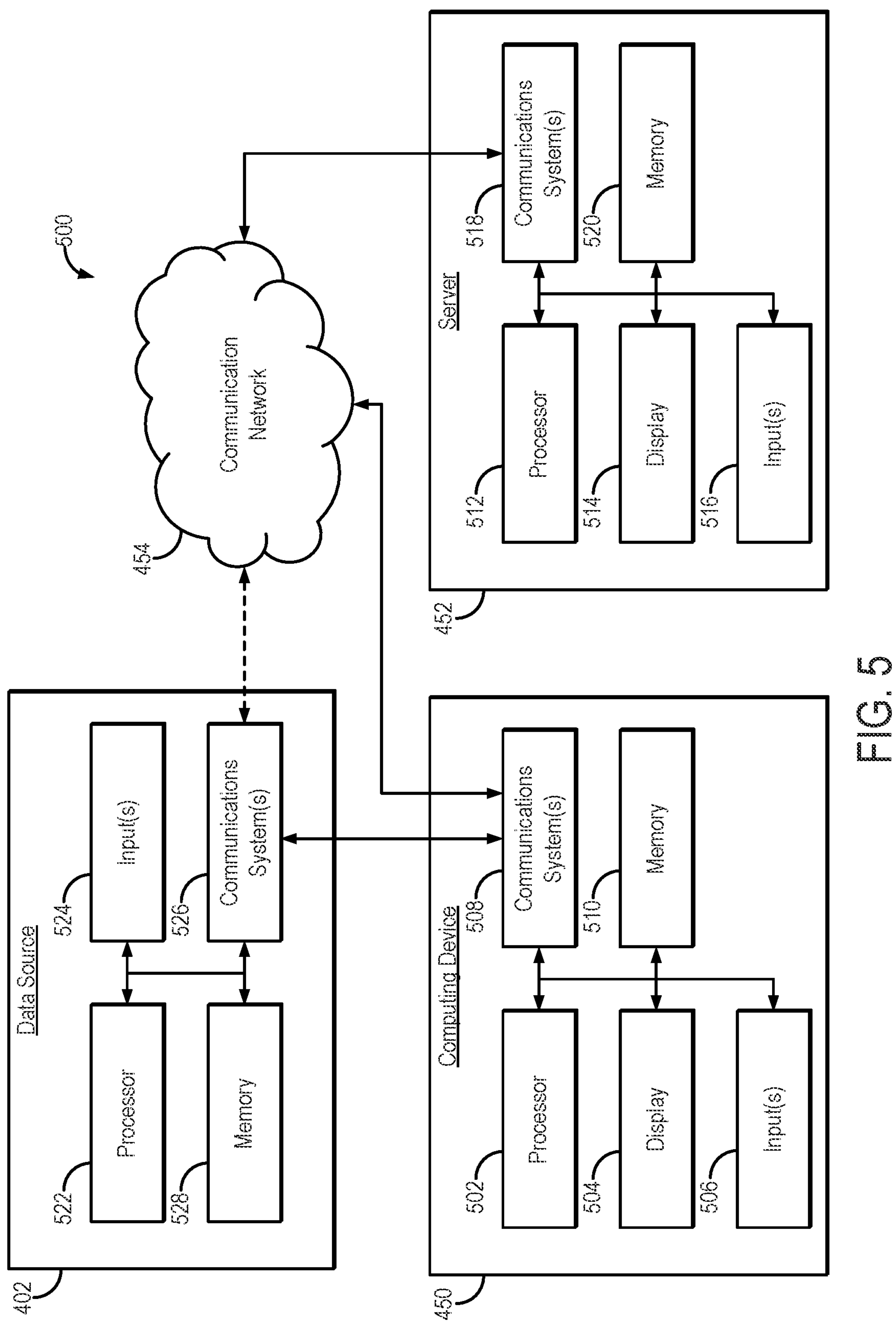
FIG. 5 is a block diagram of example components of the shear wave phase velocity estimation system of FIG. 4.

Referring now to FIG. 5, an example of hardware 500 that can be used to implement data source 402, computing device 450, and server 452 in accordance with some embodiments of the systems and methods described in the present disclosure is shown. As shown in FIG. 5, in some embodiments, computing device 450 can include a processor 502, a display 504, one or more inputs 506, one or more communication systems 508, and/or memory 510. In some embodiments, processor 502 can be any suitable hardware processor or combination of processors, such as a central processing unit ("CPU"), a graphics processing unit ("GPU"), and so on. In some embodiments, display 504 can include any suitable display devices, such as a computer monitor, a touchscreen, a television, and so on. In some embodiments, inputs 506 can include any suitable input devices and/or sensors that can be used to receive user input, such as a keyboard, a mouse, a touchscreen, a microphone, and so on.

In some embodiments, communications systems 508 can include any suitable hardware, firmware, and/or software for communicating information over communication network 454 and/or any other suitable communication networks. For example, communications systems 508 can include one or more transceivers, one or more communication chips and/or chip sets, and so on. In a more particular example, communications systems 508 can include hardware, firmware and/or software that can be used to establish a Wi-Fi connection, a Bluetooth connection, a cellular connection, an Ethernet connection, and so on.

In some embodiments, memory 510 can include any suitable storage device or devices that can be used to store instructions, values, data, or the like, that can be used, for example, by processor 502 to present content using display 504, to communicate with server 452 via communications system(s) 508, and so on. Memory 510 can include any suitable volatile memory, non-volatile memory, storage, or any suitable combination thereof. For example, memory 510 can include RAM, ROM, EEPROM, one or more flash drives, one or more hard disks, one or more solid state drives, one or more optical drives, and so on. In some embodiments, memory 510 can have encoded thereon, or otherwise stored therein, a computer program for controlling operation of computing device 450. In such embodiments, processor 502 can execute at least a portion of the computer program to present content (e.g., images, user interfaces, graphics, tables), receive content from server 452, transmit information to server 452, and so on.

In some embodiments, server 452 can include a processor 512, a display 514, one or more inputs 516, one or more communications systems 518, and/or memory 520. In some embodiments, processor 512 can be any suitable hardware processor or combination of processors, such as a CPU, a GPU, and so on. In some embodiments, display 514 can include any suitable display devices, such as a computer monitor, a touchscreen, a television, and so on. In some embodiments, inputs 516 can include any suitable input devices and/or sensors that can be used to receive user input, such as a keyboard, a mouse, a touchscreen, a microphone, and so on.

In some embodiments, communications systems 518 can include any suitable hardware, firmware, and/or software for communicating information over communication network 454 and/or any other suitable communication networks. For example, communications systems 518 can include one or more transceivers, one or more communication chips and/or chip sets, and so on. In a more particular example, communications systems 518 can include hardware, firmware and/or software that can be used to establish a Wi-Fi connection, a Bluetooth connection, a cellular connection, an Ethernet connection, and so on.

In some embodiments, memory 520 can include any suitable storage device or devices that can be used to store instructions, values, data, or the like, that can be used, for example, by processor 512 to present content using display 514, to communicate with one or more computing devices 450, and so on. Memory 520 can include any suitable volatile memory, non-volatile memory, storage, or any suitable combination thereof. For example, memory 520 can include RAM, ROM, EEPROM, one or more flash drives, one or more hard disks, one or more solid state drives, one or more optical drives, and so on. In some embodiments, memory 520 can have encoded thereon a server program for controlling operation of server 452. In such embodiments, processor 512 can execute at least a portion of the server program to transmit information and/or content (e.g., data, images, a user interface) to one or more computing devices 450, receive information and/or content from one or more computing devices 450, receive instructions from one or more devices (e.g., a personal computer, a laptop computer, a tablet computer, a smartphone), and so on.

In some embodiments, data source 402 can include a processor 522, one or more inputs 524, one or more communications systems 526, and/or memory 528. In some embodiments, processor 522 can be any suitable hardware processor or combination of processors, such as a CPU, a GPU, and so on. In some embodiments, the one or more inputs 524 are generally configured to acquire data, images, or both, and can include an ultrasound system. Additionally or alternatively, in some embodiments, one or more inputs 524 can include any suitable hardware, firmware, and/or software for coupling to and/or controlling operations of an ultrasound system. In some embodiments, one or more portions of the one or more inputs 524 can be removable and/or replaceable.

Note that, although not shown, data source 402 can include any suitable inputs and/or outputs. For example, data source 402 can include input devices and/or sensors that can be used to receive user input, such as a keyboard, a mouse, a touchscreen, a microphone, a trackpad, a trackball, and so on. As another example, data source 402 can include any suitable display devices, such as a computer monitor, a touchscreen, a television, etc., one or more speakers, and so on.

In some embodiments, communications systems 526 can include any suitable hardware, firmware, and/or software for communicating information to computing device 450 (and, in some embodiments, over communication network 454 and/or any other suitable communication networks). For example, communications systems 526 can include one or more transceivers, one or more communication chips and/or chip sets, and so on. In a more particular example, communications systems 526 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 528 can include any suitable storage device or devices that can be used to store instructions, values, data, or the like, that can be used, for example, by processor 522 to control the one or more inputs 524, and/or receive data from the one or more inputs 524; to images from data; present content (e.g., images, a user interface) using a display; communicate with one or more computing devices 450; and so on. Memory 528 can include any suitable volatile memory, non-volatile memory, storage, or any suitable combination thereof. For example, memory 528 can include RAM, ROM, EEPROM, one or more flash drives, one or more hard disks, one or more solid state drives, one or more optical drives, and so on. In some embodiments, memory 528 can have encoded thereon, or otherwise stored therein, a program for controlling operation of data source 402. In such embodiments, processor 522 can execute at least a portion of the program to generate images, transmit information and/or content (e.g., data, images) to one or more computing devices 450, receive information and/or content from one or more computing devices 450, receive instructions from one or more devices (e.g., a personal computer, a laptop computer, a tablet computer, a smartphone, etc.), and so on.

The present disclosure has described one or more preferred embodiments, and it should be appreciated that many equivalents, alternatives, variations, and modifications, aside from those expressly stated, are possible and within the scope of the invention.

The invention claimed is:

1. A method for generating shear wave phase velocity data from ultrasound data obtained with an ultrasound system, the method comprising:

(a) accessing ultrasound data with a computer system, the ultrasound data being representative of shear wave motion in a region-of-interest in a subject;

(b) generating time-frequency-space domain data with the computer system by applying a Stockwell transform to the ultrasound data, wherein the Stockwell transform is a generalized Stockwell transform that implements a generalized window function, wherein the generalized window function includes a scaling factor that changes a width of the generalized window function and controls time-frequency resolution by altering a number of oscillations in the generalized window function;

(c) generating a slant-phase function from the time-frequency-space domain data using the computer system;

(d) computing slant-phase amplitude values with the computer system using the slant-phase function;

(e) generating phase velocity dispersion curve data from the slant-phase amplitude values using the computer system, wherein the phase velocity dispersion curve data is generated over an extended frequency bandwidth that enables differentiation between soft tissues in the region-of-interest in the subject; and (f) displaying the phase velocity dispersion curve data as a phase velocity map on a display system, wherein the phase velocity map depicts a spatial distribution of measured shear wave phase velocity values within the region-of-interest.

2. The method of claim 1, wherein the generalized window function is a generalized Stockwell transform having a form that includes a plurality of scaling factors, wherein the plurality of scaling factors control time-frequency resolution of the generalized Stockwell transform.

3. The method of claim 1, wherein generating the phase velocity dispersion curve data comprises:

determining maximum values of the slant-phase amplitude values over a range of steering group velocities;

generating frequency-wavenumber pairs based on the maximum values of the slant-phase amplitude values; and generating the phase velocity dispersion curve data based on the frequency-wavenumber pairs.

4. The method of claim 3, wherein the phase velocity dispersion curve data are generated using peaks in a distribution of the frequency-wavenumber pairs.

5. The method of claim 4, wherein the peaks in the distribution of the frequency-wavenumber pairs are determined by searching in an orthogonal direction along a wavenumber-direction.

6. The method of claim 4, wherein the phase velocity dispersion curve data are generated according to $c(f)=f/k$ using the peaks in the distribution of the frequency-wavenumber pairs, where $c(f)$ is the phase velocity dispersion curve data, $f$ is a frequency value in the frequency-wavenumber pairs, and $k$ is a wavenumber value in the frequency-wavenumber pairs.

7. The method of claim 1, further comprising generating mechanical property data from the phase velocity dispersion curve data.

8. The method of claim 7, wherein the mechanical property data comprise a mechanical property map that depicts a spatial distribution of mechanical property values in the region-of-interest in the subject.

9. The method of claim 8, wherein the mechanical property map depicts a spatial distribution of viscoelastic property values in the region-of-interest in the subject.

10. The method of claim 1, wherein the ultrasound data are representative of two-dimensional shear wave particle velocity motion data.

11. The method of claim 1, wherein the slant-phase function is generated for a selected frequency range over the time-frequency-space domain data by:

determining a series of complex-valued functions of time and space; and taking slant slices of the series of complex-valued functions for a selected frequency and steering group velocity.

12. The method of claim 1, wherein the ultrasound data comprise three-dimensional ultrasound data.

13. A method for generating shear wave phase velocity data from elastography data obtained with an imaging system, the method comprising:

(a) accessing elastography data with a computer system, the elastography data being representative of shear wave motion in a region-of-interest in a subject;

(b) generating time-frequency-space domain data with the computer system by applying a Stockwell transform to the elastography data, wherein the Stockwell transform is a generalized Stockwell transform that implements a generalized window function, wherein the generalized window function includes a scaling factor that changes a width of the generalized window function and controls time-frequency resolution by altering a number of oscillations in the generalized window function;

(c) generating a slant-phase function from the time-frequency-space domain data using the computer system;

(d) computing slant-phase amplitude values with the computer system using the slant-phase function;

(e) generating phase velocity dispersion curve data from the slant-phase amplitude values using the computer system, wherein the phase velocity dispersion curve data is generated over an extended frequency bandwidth that enables differentiation between soft tissues in the region-of-interest in the subject;

(f) generating mechanical property data from the phase velocity dispersion curve data; and (g) displaying the mechanical property data as a mechanical property map on a display system, wherein the mechanical property map depicts a spatial distribution of viscoelastic property values in the region-of-interest.

14. The method of claim 13, wherein the elastography data are magnetic resonance elastography data and the imaging system is a magnetic resonance imaging system.

15. The method of claim 13, wherein the elastography data are optical coherence elastography data and the imaging system is an optical coherence tomography system.

16. The method of claim 13, wherein generating the phase velocity dispersion curve data comprises:

determining maximum values of the slant-phase amplitude values over a range of steering group velocities;

generating frequency-wavenumber pairs based on the maximum values of the slant-phase amplitude values; and generating the phase velocity dispersion curve data based on the frequency-wavenumber pairs.

17. The method of claim 16, wherein the phase velocity dispersion curve data are generated using peaks in a distribution of the frequency-wavenumber pairs.

18. The method of claim 17, wherein the peaks in the distribution of the frequency-wavenumber pairs are determined by searching in an orthogonal direction along a wavenumber-direction.

19. The method of claim 13, wherein the elastography data are representative of two-dimensional shear wave particle velocity motion data.

20. The method of claim 13, wherein the slant-phase function is generated for a selected frequency range over the time-frequency-space domain data by:

determining a series of complex-valued functions of time and space; and taking slant slices of the series of complex-valued functions for a selected frequency and steering group velocity.

21. The method of claim 13, wherein the elastography data comprise three-dimensional elastography data.

22. The method of claim 21, further comprising generating a phase velocity map based on the phase velocity dispersion curve data, wherein the phase velocity map depicts a spatial distribution of measured shear wave phase velocity values within the region-of-interest.

* * * * *